United States Patent [19]

Schechter et al.

[11] Patent Number: 5,309,922
[45] Date of Patent: May 10, 1994

[54] RESPIRATORY SOUND ANALYZER FOR USE IN HIGH NOISE ENVIRONMENTS

[75] Inventors: Gary L. Schechter, Norfolk; Robert F. Coleman, Virginia Beach, both of Va.

[73] Assignee: Center for Innovative Technology, Herndon, Va.

[21] Appl. No.: 948,677

[22] Filed: Sep. 21, 1992

[51] Int. Cl.$^5$ .............................. A61B 5/103
[52] U.S. Cl. ................... 128/721; 128/739; 128/782
[58] Field of Search ............... 128/715–716, 128/721, 774, 782, 901, 739

[56] References Cited

U.S. PATENT DOCUMENTS

| | | | |
|---|---|---|---|
| 3,656,474 | 4/1972 | Gentry et al. | 128/721 X |
| 4,437,473 | 3/1984 | Mollan | 128/774 X |
| 4,672,977 | 6/1987 | Kroll | 128/715 |
| 4,784,154 | 11/1988 | Shirley et al. | 128/715 |
| 4,951,678 | 8/1990 | Joseph et al. | 128/715 X |
| 4,967,760 | 11/1990 | Bennett, Jr. et al. | 128/715 |

*Primary Examiner*—Angela D. Sykes
*Attorney, Agent, or Firm*—Whitham & Marhoefer

[57] ABSTRACT

A respiratory sound analyzer system for use in the noisy ambient environments, such as in medical transport vehicles including helicopters, boats, aircraft, ambulances, and other vehicles, as well as at fire scenes, disasters, sporting events, rock concerts, and the like, includes an array of miniature accelerometers which are connected to the chest of a patient. Rather than relying on traditional auscultation, the on-board personnel will analyze a conditioned signal on a display screen or other device to monitor a patient's breathing patterns. Successive signals may be stored and compared with each other to determine a deterioration in a patient's breathing pattern, and signals may also be compared with stored normal and abnormal breathing signals. Ambient noise effects can be reduced or eliminated from the sensed breathing signal by a number of means. For example, the accelerometers can be heavily padded to deaden impinging sound waves, signals from accelerometers placed on the patient at locations where respiratory sounds will not be detected can be subtracted from the signals from accelerometers on the patient's chest, and filters can be used to isolate breath sounds from ambient noises.

14 Claims, 4 Drawing Sheets

RESPIRATORY SOUND ANALYZER FOR USE IN HIGH NOISE ENVIRONMENTS

BACKGROUND OF THE INVENTION

1. Field of the Invention

The present invention generally relates to devices used to detect and analyze respiratory sounds. More particularly, the invention is directed to a device used for the identification and monitoring of a parent's breathing patterns in a noisy ambient environment such as in a medical transport helicopter, aircraft, boat, ambulance, or other vehicle, or at a fire, disaster, sporting event, rock concert, or the like.

2. Description of the Prior Art

Traditional auscultation (i.e., listening) is an unacceptable method for monitoring the breathing patterns of a patient in a noisy ambient environment such as a medical transport helicopter or an ambulance. In short, experience with stethoscopes, amplified stethoscopes, and other listening devices has shown that even trained personnel are not able to distinguish respiratory sounds of a patient when the patient is located in a noisy ambient environment.

Cottrell et al., JAMA, 262:1653–1656 (1989), reported that during a one year study of medical emergencies on a commercial airline, the stethoscope was used in 80% of the instances when the on-board medical kit was required. However, a later letter to the Editor of JAMA by Bishop, JAMA, 263:233 (1990), and a reply by Cottrell and Kohn, JAMA, 263:233 (1990), indicated that in-flight auscultation attempts were unsuccessful due to the amount of ambient noise in the aircraft cabin. Cottrell and Kohn noted that ambient noise levels on board a commercial aircraft generally are low frequency, range upward to 65 dB [sic] and may approach 90 dB. They state that "At these levels, any worthwhile auscultation may be impossible, regardless of stethoscope type".

Hunt et al., JAMA, 265:1992–1994 (1991), reported that in no instances of in-flight experimental listening to recorded breath sounds emanating from the chest cavity of a resuscitation training manikin were medical personnel able to determine whether or not any breath sounds were present. This was true whether the in-flight nurses used conventional or amplified stethoscopes. Hunt et al. concluded that "Further research to develop new methods of breath sound assessment during air medical transport is urgently needed and will require the cooperative efforts of audiologists, engineers, air medical transport professionals, and physicians".

Similar poor results with stethoscopes were reported in Shenai, "Sound levels for neonates in transit", J. Pediat., 90:811–812 (1977).

Medical emergencies occur in a wide range of situations. Often, attending physicians or other medical emergency personnel must begin treatment of patients in less than ideal situaffons where ambient noise can impair the ability to detect audible respiratory sounds. Because breathing is a basic requirement of life itself, and often needs to be monitored in many medical emergencies, it would be advantageous to have equipment which allows for accurate detection and monitoring of a patient's breathing patterns. The above articles clearly indicate that present techniques of using stethoscopes is unsuitable. There is a need for an alternative device for detecting breathing signals.

SUMMARY OF THE INVENTION

It is an object of this invention to provide a respiratory sound analyzer that can be used by attending personnel to monitor breathing by a patient in a noisy ambient environment such as in a medical transport plane, helicopter, or ambulance, or at a fire, disaster, sporting event, rock concert, or the like.

It is another object of this invention to provide a respiratory sound analyzer that presents a visual signal representative of a patient's breathing patterns to attending personnel.

It is another object of this invention to provide a respiratory sound analyzer that reduces or eliminates the ambient noise from a detected respiratory sound signal.

It is yet another object of this invention to provide an audible and/or visible alarm when a patient's breathing pattern changes from preset parameters, or from the patient's initial breathing pattern as recorded when the device is first fitted to the patient.

According to the invention, a respiratory sound analyzer utilizes an array of miniature accelerometers to detect physical vibrations of a patient's chest cavity. The signal produced by the accelerometers is then presented graphically on a cathode ray tube (CRT) screen, strip chart, printout, or by some other means which allows attending medical personnel to visually analyze the patient's breathing. The graphic presentation of the patient's breathing avoids the pitfalls of using stethoscopes and amplified stethoscopes where attending medical personnel are forced to attempt to mentally separate an audible signal they hear for a patient's breathing from background noise in the ambient environment.

The respiratory sound analyzer also includes a number of elements which reduce or eliminate any effects the ambient noise may have on the array of accelerometers. For example, sound dampening material can be positioned around the accelerometers to dampen impinging ambient sound waves. A second array of accelerometers could be placed on the patient close by the chest where respiratory sounds will be picked up, but where such sounds would not be present. The patient's shoulder may be an ideal location. The output from this second array of accelerometers represents the bodily vibration of the patient in response to vehicle movement and the vehicle propulsion system (e.g., engines, rotors, etc.). The output from the second array of accelerometers would be subtracted from the output of the accelerometers placed on the patient's chest, thereby ensuring that the attending personnel observe a respiratory sound signal that is not grossly modified by vibratory effects of the medical transport vehicle. Furthermore, a filter could be used to isolate respiratory sounds from ambient artifacts in the breathing signal produced by the accelerometers on the patient's chest.

The respiratory sound analyzer is also designed to store detected respiratory sound signals such that they can be compared with signals detected at a later time interval or compared with a library of normal or abnormal sounds. When the patient is first connected, a baseline respiratory sound signal for the patient's breathing can be established. When the patient is in transit, his or her breathing patterns can be analyzed and compared with the baseline signal to detect deterioration. Hence, conditions such as a pneumothorax which gets progressively worse with time can be identified. An audible or visual alarm signal can be provided when the subsequent signals are significantly different from previous breathing patterns. Furthermore, use of a library of normal and abnormal breathing patterns would help in identifying problems with a patient's breathing which can allow earlier treatment while the parent is in transit.

BRIEF DESCRIPTION OF THE DRAWINGS

The foregoing and other objects, aspects and advantages wig be better understood from the following detailed description of a preferred embodiment of the invention with reference to the drawings, in which.

DETAILED DESCRIPTION OF THE PREFERRED EMBODIMENTS OF THE INVENTION

Figure 1:
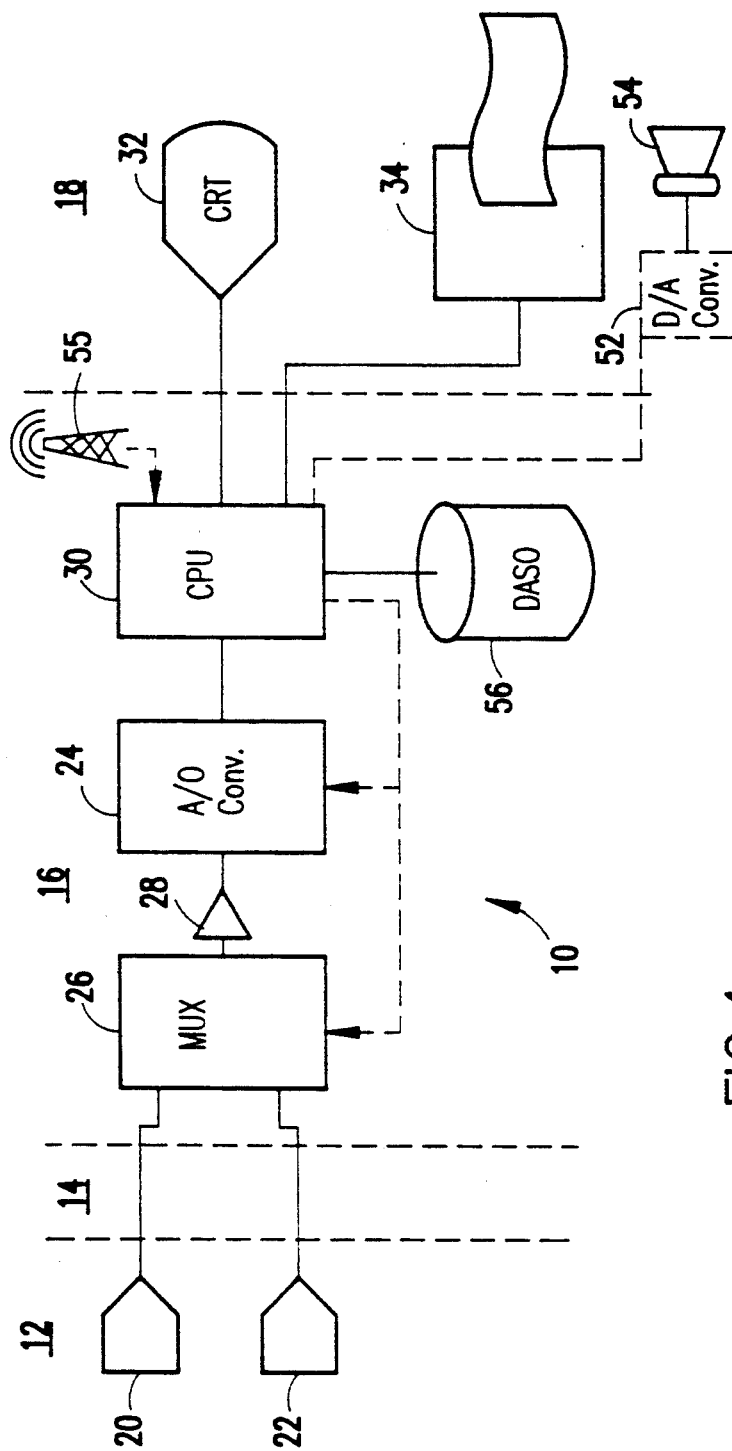
FIG. 1 is a block diagram showing the basic components of the respiratory sound analyzer.

Referring now to the drawings, and more particularly to FIG. 1, there is shown in block diagram the respiratory sound analyzer 10 according to the invention. The respiratory sound analyzer 10 comprises four principal parts: the sensing transducer 12, the ambient noise attenuation means 14, a central processor 16, and a readout device 18. A basic principle of the invention is that attending medical personnel visually analyze a graphic signal representative of the patient's breathing patterns on the readout device 18, rather than attempt to mentally identify audible signals produced during a patient's breathing from a complex, noisy ambient environment.

The transducer 12 comprises arrays of accelerometers 20 and 22 which are placed on the outside surface of a patient's chest. Each array 20 and 22 preferably includes two or more accelerometers which are positioned at different locations on the patient's chest. In a particular embodiment, there is a separate array of accelerometers 20 and 22 positioned on the right half and left half of the patient's chest. The accelerometers in the arrays 20 and 22 produce electrical signals corresponding to the acoustic patterns of the patient's breathing. Accelerometers are used as the transducers because they are in effect "contact microphones" sensing physical vibration rather than sound waves per se. Accelerometers typically have a high signal-to-noise (S/N) ratio which results in a reduced amount of ambient noise being picked up by these devices. However, in medical transport vehicles, such as helicopters, aircraft, boats and ambulances, the ambient noise can be very high; thus, the respiratory sound analyzer 10 includes an ambient noise attenuation means 14.

The central processor 16 includes several components. The first of these is an analog-to-digital (A/P) converter 24 which is connected via a multiplexer 26 to digitize the analog signals from the accelerometers 20 and 22. A separate A/D converter for each input may be used, thereby eliminating the need for a multiplexer. Input to the A/D converter 24 can be amplified using amplifier 28. The A/D converter 24 and the multiplexer 26 are controlled by a central processing unit (CPU) 30 which temporarily stores the digitized inputs in internal registers (not shown). The CPU 30 can be a personal computer (PC), or it can be a special purpose computer. The CPU 30 would be programmed to provide an output signal indicative of the sensed input signal of accelerometers 20 and 22 with respect to time. The CPU 30 could be programmed with algorithms to provide fast fourier transform (FFT) and other acoustic analyses.

The readout device 18 can include either or both a CRT display 32 or a chart recorder or printer 34. Visual presentation of the acoustic signals sensed by the accelerometer arrays 20 and 22 at the readout device 18 is a very important feature of this invention since attending medical personnel are not required to mentally separate audible signals that might be detected with a stethoscope from ambient noise.

The acoustic signals can be presented on the readout device 18 in many different formats. For example, the intensity of respiratory sounds could be presented in an amplitude versus time format similar to an oscilloscope display. Alternatively, frequency based spectra (e.g, intensity versus frequency, and other presentations) which bold time still could be presented so that components of a complex sound can be analyzed within a set time window. Possible permutations could include the use of successive FFT spectra, or a three dimensional or "waterfall" display to include an element of spectral change over successive time windows. It is anticipated that many other types of screen presentations of the sensed respiratory sounds can be provided at the readout device 18.

Spectra from each of the accelerometers in the arrays 20 and 22 might be individually presented on the CRT 32 for analysis or the output of all the accelerometers in the arrays 20 and 22 might be presented simultaneously in a split screen format for comparison.

A storage device 56, shown as a direct access storage device (DASD), stores respiratory signals from the A/D converter 24 in memory so that they may be analyzed at a later time. Storage of respiratory sound signals is another very important part of this invention because it allows the respiratory sound analyzer 10 to perform an ongoing monitoring function. In emergencies, knowledge of changes in a patient's condition over time can be critical to proper treatment. A baseline respiratory sound signal can be established when the accelerometer arrays 20 and 22 are first connected to the patient. The baseline respiratory signal might be measured before the patient is transported in an emergency vehicle. Respiratory sounds detected at a later time during transport could then be compared with the baseline respiratory sound signal to determine if there is a significant difference. A visual presentation of the comparison of signals can be provided on the CRT 32 in the form a side-by-side window or split-screen presentation of the earlier spectra and later spectra or an overlay presentation of the earlier spectra and later spectra. Many conditions, such as a pneumothorax, become progressively worse with time, and it would be beneficial for the respiratory sound analyzer to identify these conditions for the attending medical personnel. This can be accomplished with an audible alarm signal produced at speaker 54 or a visual alarm signal produced at CRT 32.

Other types of comparisons can also be made using the respiratory sound analyzer 10 of the present invention. For example, rather than comparing all spectra to a baseline spectra, the later recorded spectra can be compared with earlier recorded spectra per se, not just the baseline spectra. Significant differences between the two spectra can be identified on the CRT 32 and emergencies can be indicated using the speaker 54 and the CRT 32.

Another example of a useful comparison would be to provide a split-screen or overlay comparison on the CRT 32 of the acoustic signals detected on the right half of the chest using the accelerometer array 20 versus the acoustic signals detected on the left half of the chest using the accelerometer array 22. Differences between discrete signals detected by accelerometers on one side of the chest from the corresponding signals detected on the other side can highlight respiratory problems of the patient to attending medical personnel so that treatment can begin in transit. The CRT 32 might also display a difference signal where the spectrum from an accelerometer on the right half of the chest is subtracted from the corresponding signal on the left half of the chest, or vice versa. The difference signal may provide an important measure in evaluating the patient's breathing patterns.

Furthermore, the storage device 56 can include stored pattern recognition algorithms or templates which represent normal and abnormal breathing. The sensed respiratory sounds from accelerometer arrays 20 and 22 could be compared with normal and abnormal breathing signals, and the comparison could be presented visually as a split-screen or overlay presentation on CRT 32. An audible alarm signal may be produced at speaker 54 or a visual alarm signal may be produced at CRT 32 if abnormal breathing of a patient is identified from a comparison of the sensed respiratory sounds with the stored pattern recognition algorithms or templates. Moreover, the CPU 30 could be programmed to cause the CRT 32 to display treatment procedures to attending medical personnel for particular abnormal conditions which are identified.

All information provided on CRT 32 could also be provided by the printer or chart recorder 34. An advantage of the printer or chart recorder 34 would be that a tangible record could be produced for the patient's case history.

All the information provided at readout device 18 can be transmitted to physicians located at a remote hospital using a radio transmitter or cellular telephone 55 so that preparations for the incoming patient can begin immediately.

Figure 4:
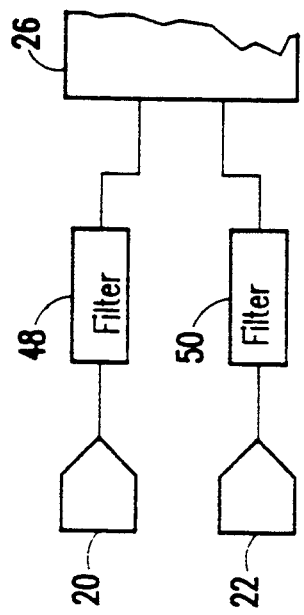
FIG. 4 is a circuit showing a filter connected in line with the accelerometers to isolate respiratory sounds from ambient artifacts.
Figure 3:
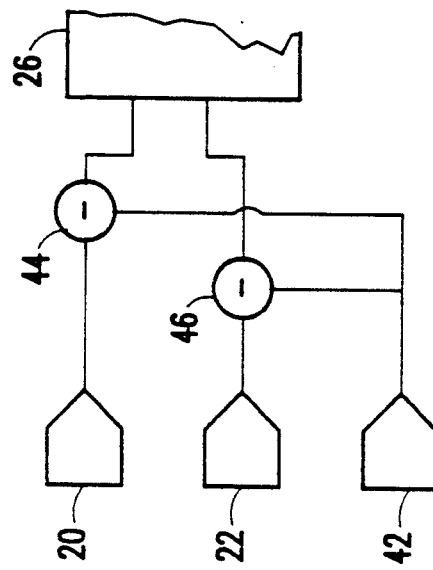
FIG. 3 is a circuit showing the subtraction of ambient vibratory signals from breathing signals.
Figure 2:
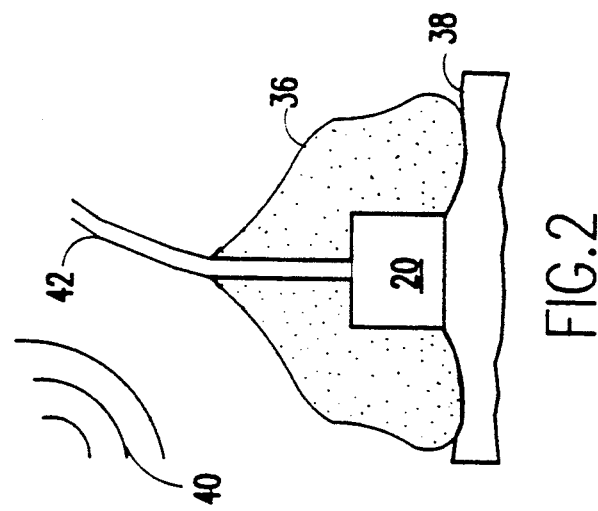
FIG. 2 is a cross-sectional side view of an accelerometer embedded in sound dampening material.

It is expected that the respiratory sound analyzer 10 win be used in extremely adverse, noisy conditions, such as on medical transport aircraft, helicopters, boats, ambulances, and other vehicles, as well as at fires, disasters, sporting events, concerts, and the like. The ambient noise, as well as the vibratory characteristics of a medical transport vehicle caused by the movement of the unit over a road, rotor and engine noise, and other environmental factors, can adversely affect the integrity of the breathing signal generated by the accelerometers 20 and 22. Therefore, the ambient noise attenuation means 14 serves an important function in assuring that the breathing signal which is analyzed at the readout device 18 closely reflects actual breathing of the patient. FIGS. 2 through 4 present alternative devices which are designed to fulfill the function of the ambient noise attenuation means 14, and these devices can be used both singly and in combination.

FIG. 2 shows the accelerometer 20 encased in a sound dampening foam 36 or other material. Baffle arrangements may also be used. The accelerometer 20 is secured to a patient's chest using a gel 38 or other suitable material. Impinging sound waves 40 from the ambient environment are dampened by the foam 36 so that the signal generated by accelerometer 20 and transmitted on wire 42 to the multiplexer 26 mainly reflects the sensed vibrations through the chest wall of the patient, rather than sound waves 40 in the ambient environment.

FIG. 3 shows an accelerometer 42 which is placed on the patient close by the chest where the respiratory sounds will be picked up by the accelerometers in arrays 20 and 22, but where such sounds would not to present. The shoulder or arm of the patient may be suitable locations for the accelerometer 42. The accelerometer 42 could be identical to the accelerometers in arrays 20 and 22 that are placed on the patient's chest and would have similar signal generating characteristics. The output from the accelerometer 42 would reflect the effects of vibrations of the patient's body in response to vehicle movement and the propulsion system (e.g., engine, rotors, etc.). The output can be viewed as vibration noise that would distort the detected signals for the patient's breathing. The signal from accelerometer 42 would be subtracted from the sensed breathing signals generated by accelerometers 20 and 22 using summer circuitry 44 and 46, or by other suitable means. Hence, the vibration noise signal is subtracted from the breathing signal to provide a signal which more accurately reflects a patient's respiratory sounds.

FIG. 4 shows filters 48 and 50 positioned to remove extraneous, unwanted noise from the signals generated by accelerometers 20 and 22. A band-pass filter could be used to perform this function and it would exhibit signal transmission characteristics as a function of frequency. The basic function of a band-pass filter is to pass wanted signals and suppress unwanted signals according to frequency. Band-pass filters operate as linear devices with the output voltage strictly proportional to input voltage at any frequency and signal level within their operating capabilities. In the instant case, a band-pass filter having the desired frequency range of normal pulmonary sounds, as the center of bandwidth frequency, between the two cutoff frequencies, should be selected as the band-pass filter required to reduce the ambient noise.

Returning to FIG. 1, it can be seen that a conditioned signal from the CPU 30 may also be audibly heard by attending medical personnel using a digital-to-analog (D/A) converter 52 and speaker or earphone 54. In this way, the traditional methods of auscultation could still be employed with the respiratory sound analyzer 10; however, the audible signals from the speaker or earphone 54 would be more identifiable to attending medical personnel because they would have been amplified 28 and ambient noise affects on the signal would have been attenuated at the ambient noise attenuation stage 14. Furthermore, the graphical presentation on CRT display 32 or chart recorder 34 would reinforce the positive identification of the audible signal from the speaker or earphone 54.

Figure 5A:
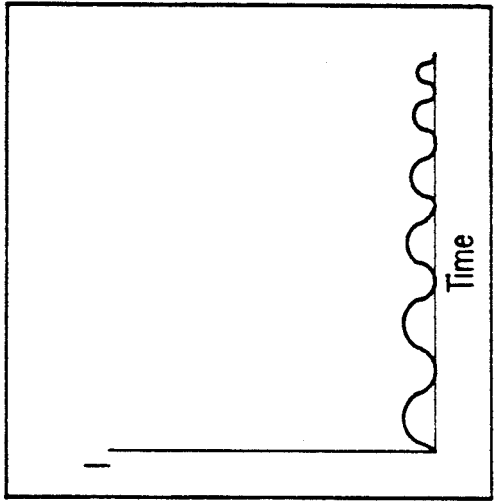
FIGS. 5a and 5b are stylized screen presentations of respiratory signals having different intensities and time durations.
Figure 5B:
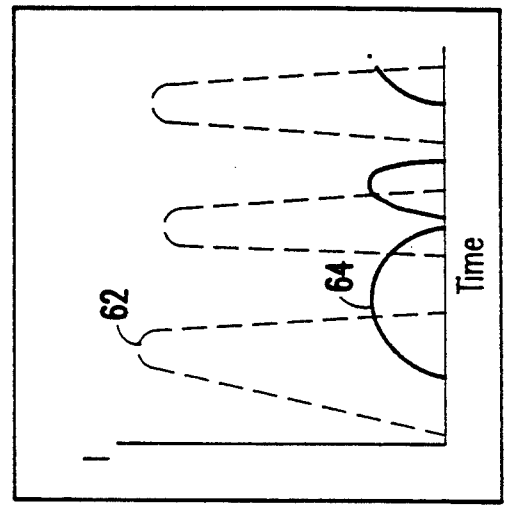
Figure 6:
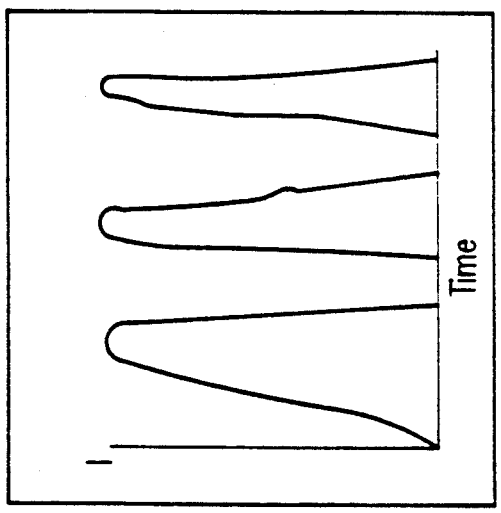
FIG. 6 is a stylized split-screen presentation of an earlier recorded respiratory signal and a later sensed respiratory signal.
Figure 7:
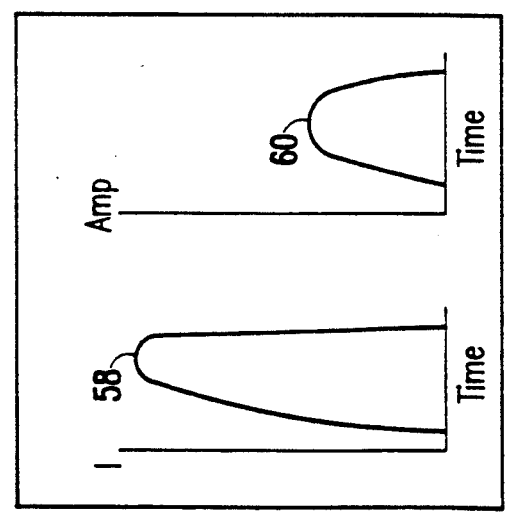
FIG. 7 is a stylized overlay presentation of a normal respiratory signal over an abnormal sensed respiratory signal.
Figure 8A:
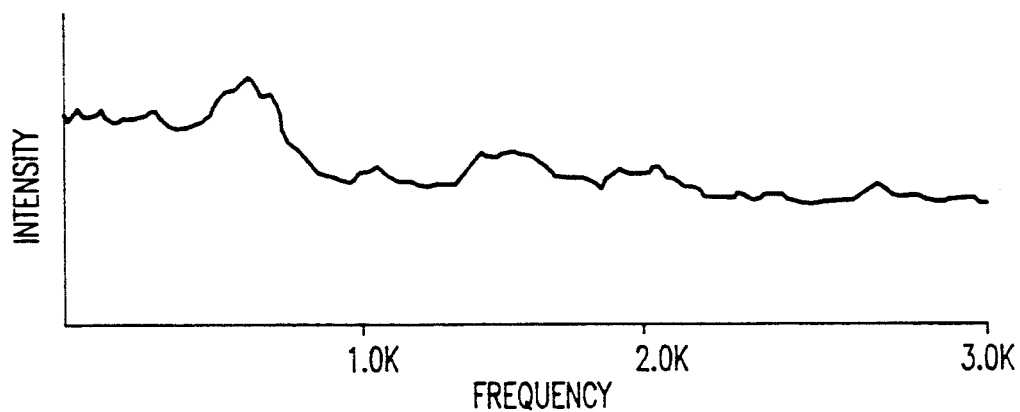
FIGS. 8a–b are stylized screen presentations of frequency based respiratory spectra.
Figure 8B:
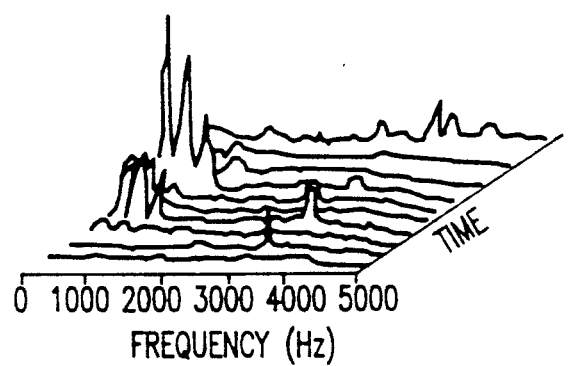

FIGS. 5a-b, 6, 7, and 8a-b are stylized displays which may be provided on CRT 32. It should be understood that these displays represent only a few examples of how visual information may be presented to attending medical personnel by the respiratory sound analyzer 10. The displays are provided to illustrate the points made above and should not be construed as limiting the manner in which respiratory sound information can be presented for analysis. FIG. 5a may represent normal breathing of a patient where strong (high intensity) signals are shown at periodic intervals over a period of time, whereas FIG. 5b may represent a detected hyperventilation situation for the patient where relatively weak (low intensity) signals are shown at relatively more frequent intervals over the same period of time. FIG. 6 shows a split-screen display where a previously stored signal 58 retrieved from storage device 56 is compared side-by-side with a currently sensed breathing signal 60. FIG. 7 shows an overlay presentation of a nominal breathing signal 62, obtained from a template stored in storage device 56, positioned over an abnormal breathing signal 64 which has been detected for the patient being monitored. FIGS. 8a and 8b show spectra where acoustic signals were processed using FFT where FIG. 8a shows an isolated frequency spectrum and FIG. 8b shows an example of a three-dimensional or waterfall display which has a time element.

While the invention has been described in terms of its preferred embodiments, those skilled in the art will recognize that the invention can be practiced with modification within the spirit and scope of the appended claims.

Having thus described our invention, what we claim as new and desire to secure by Letters Patent is as follows:

1. A respiratory sound analyzer, comprising:
    first accelerometer means adapted to be placed on the chest wall of a patient, said accelerometer means generating a breathing signal corresponding to physical vibrations of said chest wall of said patient;
    second accelerometer means adapted to be placed on said patient near said chest wall, at a location where physical vibrations caused by respiratory activity are not detected, said second accelerometer means generating an ambient signal corresponding to physical vibrations of said patient caused by the ambient environment; and
    means or subtracting said ambient signal from said breathing signal;
    processing means for processing said breathing signal and providing a graphic signal representative of said breathing signal; and
    means for visually presenting said graphic signal to attending health care personnel.

2. A respiratory sound analyzer as recited in claim 1 further comprising one of a noise dampening material and a baffle associated with said first accelerometer means.

3. A respiratory sound analyzer as recited in claim 1 further comprising a filter means for isolating respiratory sounds from ambient noise sounds in said breathing signal generated by said first accelerometer means.

4. A respiratory sound analyzer as recited in claim 1 further comprising:
    one of a noise dampening material and a baffle associated with said first accelerometer means; and
    a filter means for isolating respiratory sounds from ambient noise sounds in said breathing signal generated by said first accelerometer means.

5. A respiratory sound analyzer as recited in claim 1 wherein said first accelerometer means includes a separate array of accelerometers forth both a left side and a right side of said patient's chest.

6. A respiratory sound analyzer as recited in claim 1 wherein said means for presenting a graphic signal includes a cathode ray tube.

7. A respiratory sound analyzer as recited in claim 1 wherein said means for presenting a graphic signal includes a printer.

8. A respiratory sound analyzer as recited in claim 1 wherein said means for presenting a graphic signal includes a chart recorder.

9. A respiratory sound analyzer as recited in claim 1 wherein said processing means includes a means for storing breathing signals.

10. A respiratory sound analyzer as recited in claim 9 further comprising a means for comparing a first set of breathing signals with a second set of breathing signals.

11. A respiratory sound analyzer as recited in claim 10 wherein said first set of breathing signals are recorded from said patient at an earlier time period relative to a time period when said second set of breathing signals are recorded.

12. A respiratory sound analyzer as recited in claim 1 wherein said processing means includes a comparing means for comparing said breathing signal generated by said first accelerometer means with stored normal and normal breathing signals.

13. A respiratory sound analyzer as recited in claim 1 further comprising audible means for outputting an audible signal which corresponds with said breathing signal.

14. A respiratory sound analyzer as recited in claim 1 further comprising an analog-to-digital converter means connected to receive said breathing signal generated by said first accelerometer means and to produce a digitized signal of a sensed respiratory sound.

* * * * *